United States Patent
Lee et al.

(10) Patent No.: US 10,524,721 B2
(45) Date of Patent: Jan. 7, 2020

(54) METHODS AND SYSTEMS FOR MONITORING A PATIENT TO REDUCE THE INCIDENCE OF PRESSURE ULCERS

(71) Applicant: LIFE SUPPORT TECHNOLOGIES, INC., Tarrytown, NY (US)

(72) Inventors: Bok Lee, Wappingers Falls, NY (US); Glenn Butler, Tarrytown, NY (US)

(73) Assignee: Life Support Technologies, Inc., Tarrytown, NY (US)

( * ) Notice: Subject to any disclaimer, the term of this patent is extended or adjusted under 35 U.S.C. 154(b) by 105 days.

(21) Appl. No.: 13/867,026

(22) Filed: Apr. 19, 2013

(65) Prior Publication Data

US 2013/0281804 A1  Oct. 24, 2013

Related U.S. Application Data

(60) Provisional application No. 61/636,030, filed on Apr. 20, 2012.

(51) Int. Cl.
  *A61B 5/00* (2006.01)
  *A61G 7/057* (2006.01)
  *A61B 5/1455* (2006.01)
  *A61B 5/01* (2006.01)

(52) U.S. Cl.
  CPC ............ *A61B 5/447* (2013.01); *A61G 7/057* (2013.01); *A61B 5/01* (2013.01); *A61B 5/14551* (2013.01); *A61B 5/445* (2013.01); *A61B 5/4875* (2013.01); *A61B 5/6891* (2013.01); *A61B 5/742* (2013.01); *A61B 5/746* (2013.01); *A61B 2562/0247* (2013.01); *A61G 2203/30* (2013.01)

(58) Field of Classification Search
  CPC ... A61B 5/447; A61B 5/14551; A61B 5/6891; A61B 5/01; A61B 5/746; A61B 5/742; A61B 5/4875; A61B 5/0247; A61B 5/445
  USPC .................................................. 600/300, 301
  See application file for complete search history.

(56) References Cited

U.S. PATENT DOCUMENTS

| | | | |
|---|---|---|---|
| 2006/0183980 A1* | 8/2006 | Yang | 600/301 |
| 2008/0275349 A1 | 11/2008 | Halperin et al. | |
| 2009/0070939 A1* | 3/2009 | Hann | A61B 5/11 5/652.1 |
| 2009/0156988 A1 | 6/2009 | Ferren et al. | |

(Continued)

FOREIGN PATENT DOCUMENTS

WO  WO 2011/091517  8/2011

OTHER PUBLICATIONS

Bouten et al. "The etiology of pressure ulcers: Skin deep or muscle bound?" Archives of Physical Medicine and Rehabilitation vol. 84, Issue 4, Apr. 2003, pp. 616-619.*

(Continued)

*Primary Examiner* — Nathan J Jenness
(74) *Attorney, Agent, or Firm* — Dugan & Dugan, PC

(57) ABSTRACT

Systems, methods, and apparatus are provided for preventing and treating pressure ulcers in bedfast patients. The invention includes monitoring a bedfast patient using a sensor array disposed between a patient and a support surface, the sensor array adapted to transmit signals indicative of interfacial pressure and blood oxygen saturation levels; and a processor coupled to the sensor array and adapted to receive the signals from the sensor array to determine if an undesirable condition exists. Numerous additional aspects are disclosed.

18 Claims, 13 Drawing Sheets

(56) References Cited

U.S. PATENT DOCUMENTS

| | | | | |
|---|---|---|---|---|
| 2009/0259117 | A1* | 10/2009 | Wider | A61B 5/14551 600/323 |
| 2010/0101026 | A1 | 4/2010 | Papaioannou | |
| 2010/0312076 | A1* | 12/2010 | Bly | A61B 5/412 600/301 |
| 2010/0325796 | A1* | 12/2010 | Lachenbruch | A61F 7/02 5/423 |
| 2011/0068928 | A1 | 3/2011 | Riley et al. | |
| 2011/0263950 | A1* | 10/2011 | Larson et al. | 600/301 |
| 2011/0301432 | A1* | 12/2011 | Riley et al. | 600/300 |
| 2012/0053424 | A1* | 3/2012 | Kenalty et al. | 600/300 |
| 2013/0081208 | A1 | 4/2013 | Dyevich et al. | |

OTHER PUBLICATIONS

Hagblad et al. "A technique based on laser Doppler flowmetry and photoplethysmography for simultaneously monitoring blood flow at different tissue depths" Medical & Biological Engineering & Computing May 2010, vol. 48, Issue 5, pp. 415-422.*

Baumchen et al. "Near Infrared Spectroscopy Measurement of Sacral Tissue Oxygenation Saturation (StO2) in Healthy Volunteers Immobilized on Spine Boards" Proceedings of the 5th Annual GRASP Symposium, Wichita State University, 2009.*

Yip, M. et al. "A flexible pressure monitoring system for pressure ulcer prevention." Engineering in Medicine and Biology Society, 2009. EMBC 2009. Annual International Conference of the IEEE. 2009. 1212-1215.*

Pruitt et al. ("Interpreting Arterial Blood Gases: Easy as ABC" Nursing vol. 34, No. 8, 2004.*

International Search Report and Written Opinion of counterpart International Application No. PCT/US2013/037494 dated Aug. 1, 2013.

International Preliminary Report on Patentability and Written Opinion of counterpart International Application No. PCT/US2013/037494 dated May 14, 2015.

* cited by examiner

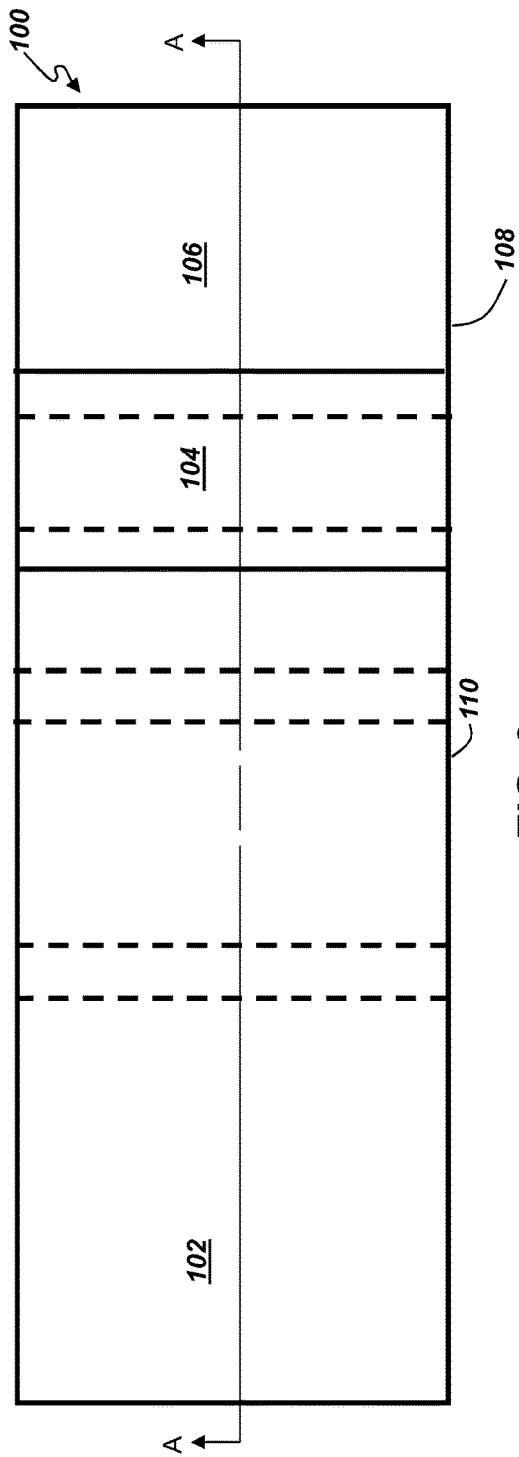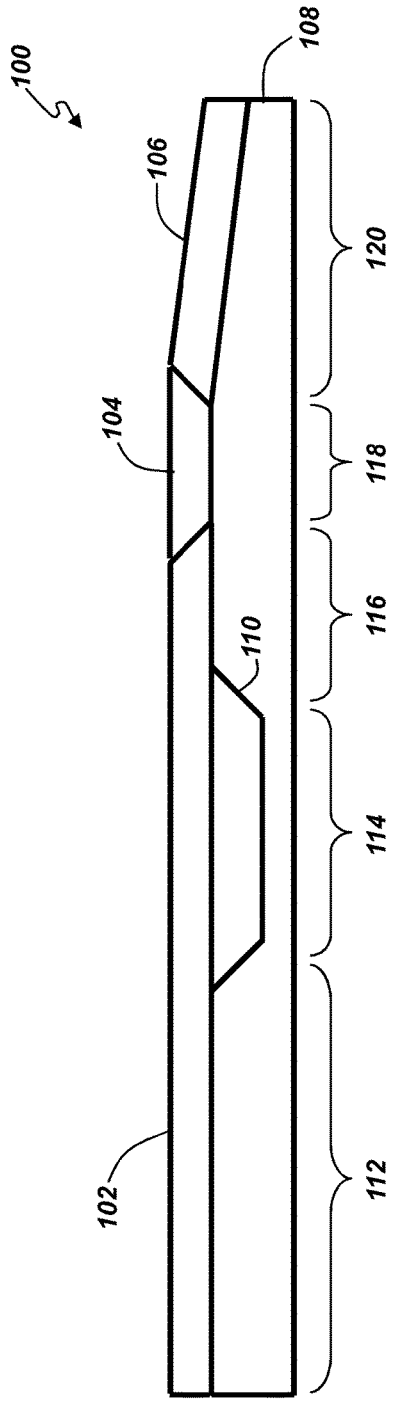

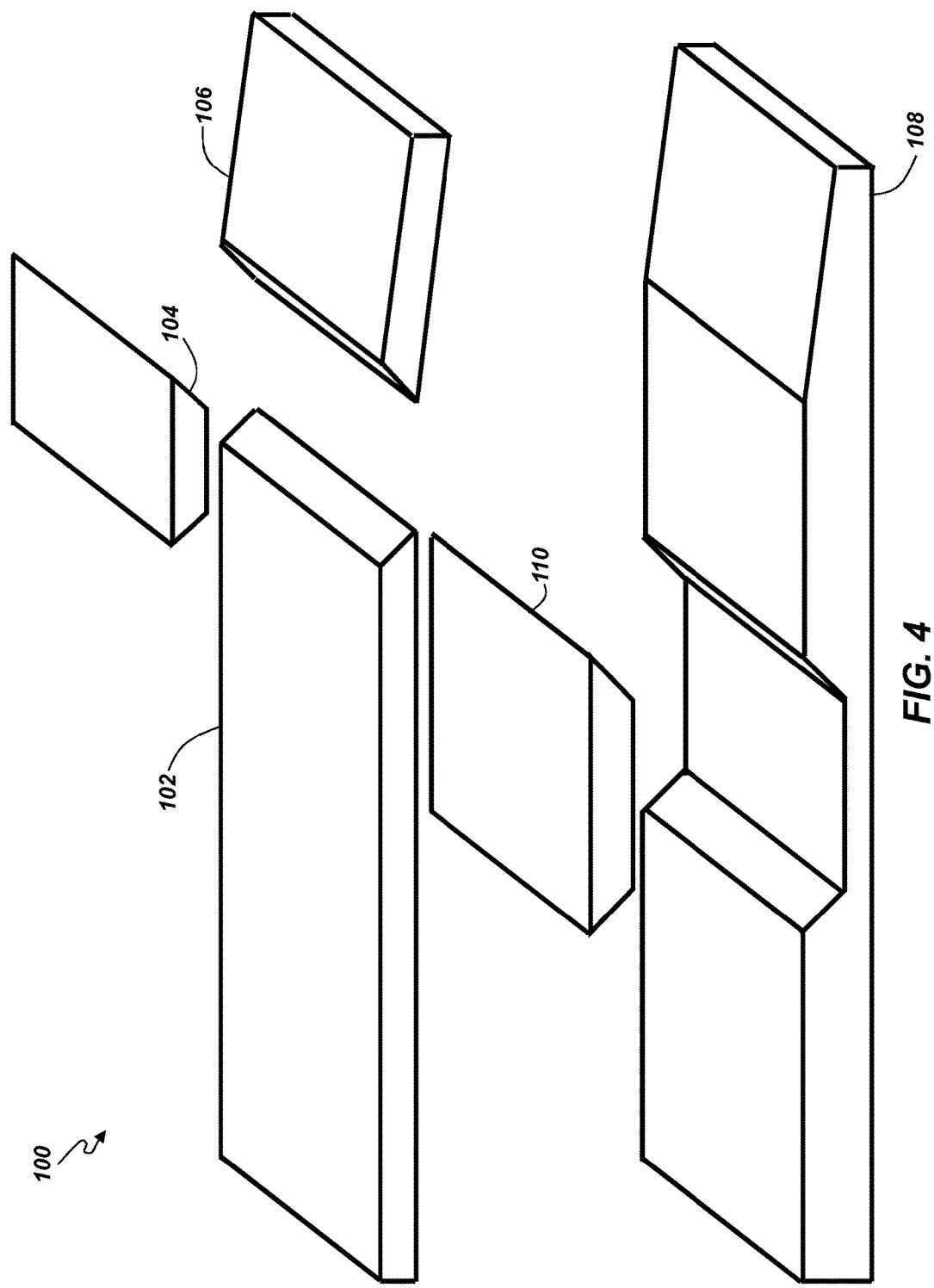

FIG. 8B BACK

FIG. 8A FRONT

METHODS AND SYSTEMS FOR MONITORING A PATIENT TO REDUCE THE INCIDENCE OF PRESSURE ULCERS

RELATED APPLICATION

The present application is related to and claims priority from U.S. Provisional Patent Application No. 61/636,030, filed on Apr. 20, 2012, titled "METHODS AND SYSTEMS FOR MONITORING A PATIENT TO REDUCE THE INCIDENCE OF PRESSURE ULCERS," which is hereby incorporated by reference herein in its entirety for all purposes.

FIELD

The present invention relates generally to patient monitoring, and more specifically to monitoring a patient to treat and reduce the incidence of pressure ulcers.

BACKGROUND

The development of pressure ulcers among hospital and nursing home patients remains one of the greatest preventable challenges to healthcare worldwide. It is estimated that in 2011 in the United States alone, costs related to the prevention and management of pressure ulcers at home and in clinical settings exceeds three billion dollars annually.

Patients immobilized and unable to move can suffer serious destruction of the skin and soft body tissue in as little as one hour. This often results in the formation of a pressure ulcer. A pressure ulcer is defined as any lesion caused by unrelieved pressure resulting in underlying tissue damage. Complications related to pressure ulcers cause an estimated 60,000 deaths in the United States annually. However, most pressure ulcers are treatable and even preventable.

Patients that have difficulty moving while in bed are at risk with the highest risk for pressure ulcer development being among diabetic, insensate, and paraplegic patients. Accordingly, dozens of mattress designs have been produced over the years to help better distribute or periodically reduce pressure on anatomical areas of the body at high risk for the development of pressure ulcers. For example, the microAIR Therapeutic Support Systems manufactured by Invacare Corporation of Cleveland, Ohio provides a pneumatic mattress with alternating zones to change the points of support.

To date however, all the scientific data that has been developed to support mattress manufacturer claims has been based on interfacial (mmHg) pressure point measurements over time using an empirical algorithm to estimate tissue ischemia in an attempt to predict pressure ulcer development.

The inventors of the present invention have determined that this approach is unreliable. Therefore, what is needed are methods and systems to determine an off-loading mattress design and/or clinical procedure that will reduce the incidence of pressure ulcers and to provide treatment for all stages (e.g., 1 through 4) of pressure ulcers.

SUMMARY

In some aspects of the invention, a system for preventing and treating pressure ulcers in bedfast patients is provided. The invention includes a system for monitoring a bedfast patient using a sensor array disposed between the patient and a support surface, the sensor array adapted to transmit signals indicative of interfacial pressure and blood oxygen saturation levels; and a processor coupled to the sensor array and adapted to receive the signals from the sensor array to determine if an undesirable condition exists.

In some other aspects of the invention, a method of preventing and treating pressure ulcers in bedfast patients is provided. The method includes monitoring a bedfast patient using a sensor array disposed between a patient and a support surface, the sensor array adapted to transmit signals indicative of interfacial pressure and blood oxygen saturation levels; and a processor coupled to the sensor array and adapted to receive the signals from the sensor array to determine if an undesirable condition exists.

In yet other aspects of the invention, a method of designing a mattress for treatment and prevention of pressure ulcers in bedfast patients is provided. The method includes disposing sensors between a test subject and an initial mattress design, the sensors adapted to transmit signals indicative of interfacial pressure and blood oxygen saturation levels; and receiving the signals from the sensors in a processor coupled to the sensors and determining from the signals if a restricted blood flow condition exists.

Other features and aspects of the present invention will become more fully apparent from the following detailed description, the appended claims and the accompanying drawings.

BRIEF DESCRIPTION OF THE DRAWINGS

FIG. 2 is a top view depicting an example mattress according to embodiments of the present invention.

FIG. 3 is a side view depicting an example mattress according to embodiments of the present invention.

FIG. 4 is an exploded perspective view depicting an example mattress according to embodiments of the present invention.

DETAILED DESCRIPTION

Figure 1:
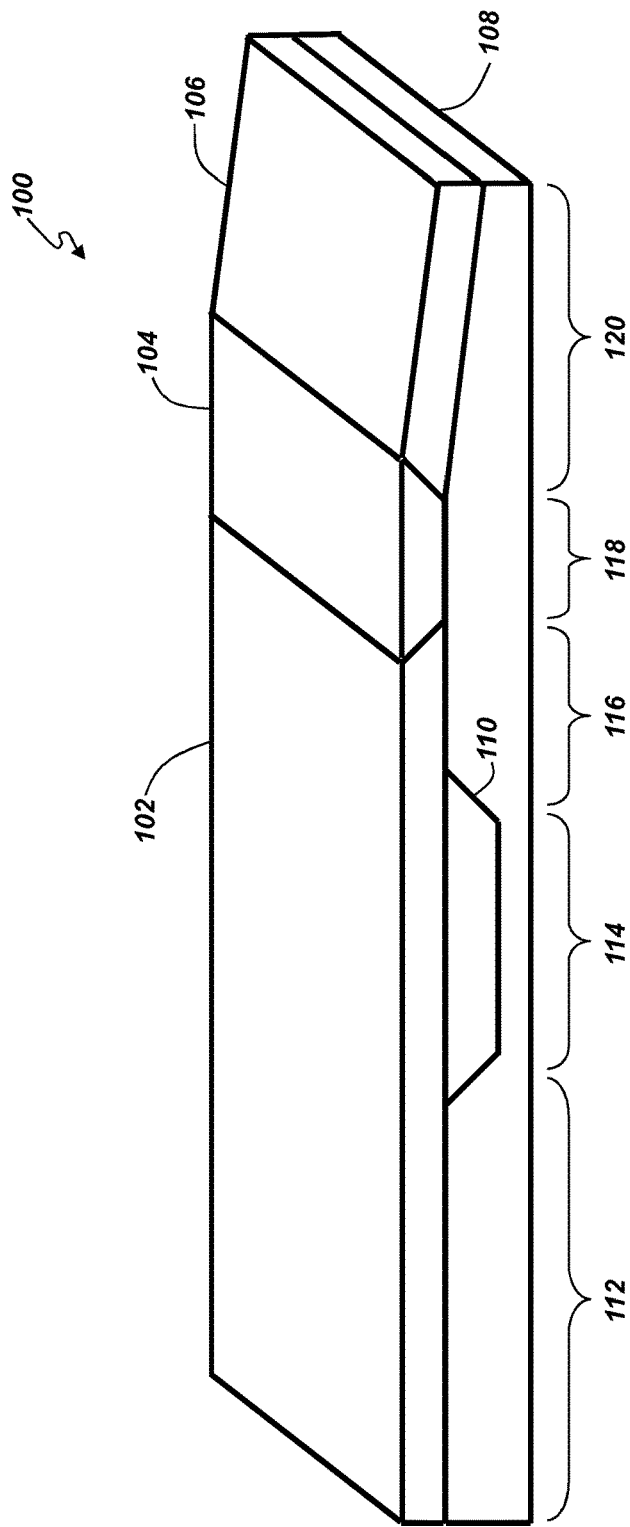
FIG. 1 is a perspective view depicting an example mattress according to embodiments of the present invention.

The present invention provides a low-cost, non-powered mattress adapted to treat and reduce the occurrence of pressure ulcers in bedfast patients by dynamically off-loading weight from critical anatomical areas. The mattress includes several zones that include material of varying densities, indention force deflection (IDF) values, and component shapes which work together to avoid restrictions in oxygenated blood flow.

Unlike prior attempts to treat and avoid pressure ulcers, the present invention does not rely on merely reducing or equalizing interfacial pressure across the entire body. The inventors of the present invention have determined that interfacial pressure measurement alone is not an accurate predictor of the development of pressure ulcers in bedfast patients and interfacial pressure alone should not be used to evaluate mattresses. Instead, the mattress of the present invention equalizes blood oxygen saturation around anatomical areas that have bony prominences to avoid ischemia which would otherwise lead to pressure ulcers. The inventors have determined that anatomical site location pressure and oxygen saturation do not necessarily inversely correlate. This means that a relatively high interfacial pressure does not necessarily result in lower tissue oxygen saturation and lower interfacial pressures does not always result in higher oxygen saturations.

Tissue ischemia and ischemia reperfusion injury are one of the primary contributors to the formation of pressure sores or ulcers. Pressure upon tissues, especially those over the bony prominences of the body can be detrimental to cellular function, particularly if incurred for prolonged periods of time. In general, damage to tissues is less likely when the pressure of the body is evenly distributed over a wide area then if the pressure is localized at, and or over some pressure point. Time is also important factor in the consideration of tissue pressure and breakdown. Lower levels of pressure maintained for long periods of time produce more tissue damage than high pressure for short periods. In other words, in some instances time may be a more detrimental factor than actual pressure. Even the intermittent relief of pressure may allow for delivery of adequate nutrients to the cellular level.

Since patients may be in bed for eight hours or more, the mattress in use becomes a significant variable in the reduction and or relief of pressure on the patient's body, particularly over bony prominences. An increase in mechanical stress (pressure and shear) decreases the availability of nutrients, such as oxygen. Long interfacial pressure periods applied to tissue decreases blood flow to the coetaneous tissue, which results in hypoxia. Hypoxia forces cells to use anaerobic pathways to produce energy, more lactic acid will accumulate, more acidosis and hydrogen ions, and more potassium becomes available around the cell. These factors lead to vasodilatation to help attract more blood and oxygen to the tissues. This is useful with a healthy cardiovascular system. However, if pressure continues, this defense mechanism will fail.

In patients with paraplegia, atherosclerosis, or cardiovascular failure, for example, the blood vessels dilate less efficiently and blood will not move into the hypoxic area. If pressure continues longer, more metabolites will accumulate and ischemia will result in cell death and necrosis. On the other hand, if the patient's position is changed after the ischemia, pressure will be released, and normal blood flow will resume. This reactive hyperemia will lead to reperfusion injury by generating free radicals. The tissue becomes more susceptible to necrosis upon repeating these events, and ultimately may become infected.

Reactive Hyperemia (RH) is a hallmark of reperfusion injury and pressure ulcer development. Thus, the mattress of the present invention includes features that may result in uneven interfacial pressure but avoids RH.

In some embodiments, the invention may use various types of foam (polyurethane, memory Foam, synthetic latex, latex, etc.) in a multi-zoned, multi-layered mattress construction to provide a relatively low pressure support environment. This allows maximum immersion, enveloping all bony prominences in a three dimensional format (length, width, and height) and to conform the mattress to the anthropometric characteristics of the human body in supine, prone, and lateral (e.g., side-laying) positions. The arrangement of the present invention also dramatically lowers vertical and horizontal shear forces while allowing the subcutaneous muscle tissue next to the bone to have the highest levels of oxygen saturation to support tissue viability for prevention and healing of any stage pressure ulcer.

Using near-infrared spectroscopy, a non-invasive method to continuously measure subcutaneous oxygen in deep muscle tissue proximate to bone, the inventors were able to determine the material types, densities, IFDs, and shapes that allowed the highest levels of oxygen saturation, particularly in tissue adjacent bony prominences. In some embodiments, five separate zones may be used to both provide firmness where the body needs support and softness to envelop bony prominences. Going from the head end of the mattress to the heel end, the five zones may include the scapular zone, the sacrum/ischium/trochanter zone, the thigh zone, the calf zone and the heel zone.

In some embodiments, the scapular zone may include an approximately 5.5" densificated polyurethane foam layer covered with an approximately 2.5" top layer of synthetic latex foam. This structure conforms to, off-loads, and equalizes the pressure on the scapular.

In some embodiments, the sacrum/ischium/trochanter zone may include an approximately 2" densificated polyurethane foam base layer, an approximately 3.5" memory foam core layer, and an approximately 2.5" synthetic latex foam top layer. This structure allows for deep immersion of the sacrum and trochanter in a supine, side-laying and various head of bed elevations (e.g., 0, 15, 30, 45 degrees). The edges of the core layer of the sacrum/ischium/trochanter zone maybe cut at angles to create a gradual density transition from the scapular zone and to the thigh zone. As will be discussed in detail below, the angled edges of the core layer of the sacrum/ischium/trochanter zone may be adapted to transfer vertical downward pressure in lateral directions. This dynamically increases the density of the adjacent zones, which in turn provides more support to the body areas contacting the increased density areas of the mattress and off-loads the pressure on the sacrum/ischium/trochanter.

In some embodiments, the thigh zone may include an approximately 5.5" densificated polyurethane foam layer covered with an approximately 2.5" top layer of synthetic latex foam. This structure conforms to, off-loads, and equalizes the pressure on the thighs.

In some embodiments, the calf zone utilizes approximately 2.5" layer of relatively higher density polyurethane foam over a base layer of approximately 5.5" of densificated polyurethane foam. This facilitates elevating the calves and off-loading the heels allowing deep tissue oxygenation to remain at base line levels.

In some embodiments, the heel zone incorporates relatively soft vertical cell polyurethane foam to envelop the heels and provide relatively low interface pressures, greatly reducing the risk of pressure ulcer formation on the pressure sensitive heels. In some embodiments, the heel zone uses approximately 2.5" layer of vertical cell polyurethane foam over a slanting base layer of approximately 5.5" of densificated polyurethane foam adjacent the calf zone that gradients down to approximately 3" thick at the heel end of the mattress.

In some embodiments, a shear liner is used to help to transfer vertical and horizontal forces away from the body by allowing the top layer to move independently of the lower components of the mattress.

Turning to FIG. 1, a perspective drawing depicting an embodiment of and example mattress 100 according to the present invention is provided. The mattress 100 may include a top layer 102, a calf pillow 104, a heel cushion 106, a base structure 108, and a core layer 110 arranged as shown. In some embodiments additional or fewer components may be included. For example, in some embodiments additional core layers may disposed at different locations such as, for example within the region of the scapular.

Figure 8:
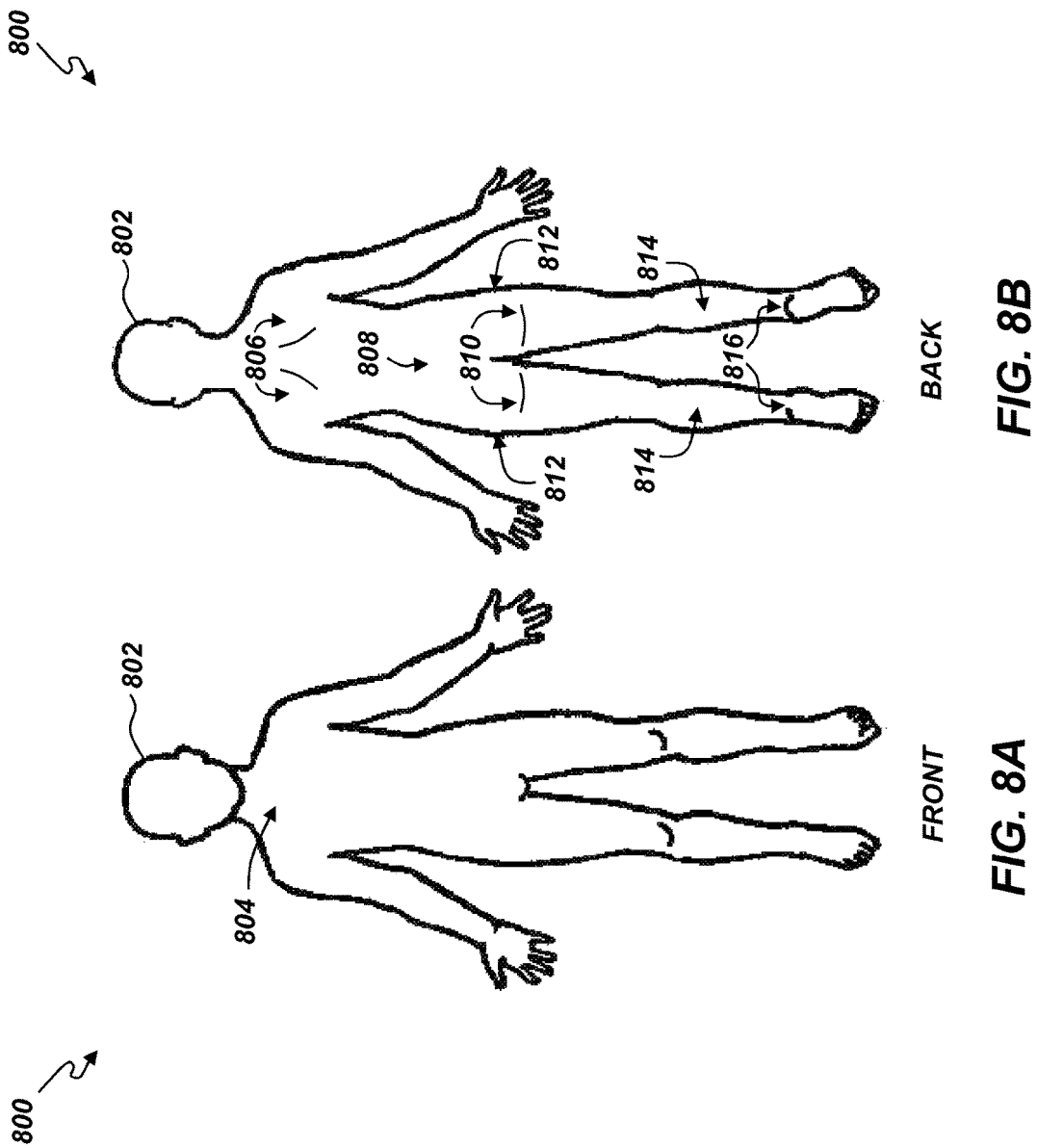
FIGS. 8A and 8B are simplified front and posterior line drawings, respectively, of a human body identifying anatomical features or areas relevant to the present invention.

The particular structure depicted in FIG. 1 results in a mattress that includes the five distinct zones discussed above. Other structures with five zones are possible as well. Further, in some embodiments, structures that result in more or fewer than five zones are possible. As indicated above, the example structure depicted in FIG. 1 includes, from the head end of the mattress 100 to the foot end of the mattress 100, a scapular zone 112, a sacrum/ischium/trochanter zone 114, a thigh zone 116, a calf zone 118 and a heel zone 120. Note that these zones correspond to anatomical features of a human body 800 as depicted in FIGS. 8A and 8B. The scapular zone 112 is designed to support the clavicle area 804 when the patient lies prone on the mattress 100 and to support the scapular area 806 when the patient lies supine on the mattress 100. The sacrum/ischium/trochanter zone 114 is designed to support the sacrum area 808 and the ischium area 810 when the patient lies supine on the mattress 100 and to support the trochanter area 812 when the patient is side-laying. The thigh zone 116 is designed to support the patient's thighs. The calf zone 118 is designed to support the patient's calves 814 so that the heels 816 are off-loaded. The heel zone 120 is designed to conform to the patient's heels 816.

Turning now to FIGS. 2 through 4, a top elevation view, a side elevation view, and an exploded perspective view respectively, of the example embodiment mattress 100 are provided. Note that the same reference numbers from FIG. 1 are used to indicate the same components as they appear in FIGS. 2 through 4 and that the drawings are not to scale. The following chart provides example dimension ranges, materials, IFD ranges, and density ranges for each of the five components of the example mattress 100.

| Component | Ref Num | Material | Density Range Nom/Max (lbs/ft³) | IFD Range @25% Compress Nom/Max (lbs) | Outside Dimensions Nom/Min/Max (inches) |
|---|---|---|---|---|---|
| Top Layer | 102 | synthetic latex foam | 3.65 to 3.85 2.95 to 4.62 | 20 to 25 16 to 30 | 2.5 × 35 × 54 2 × 28 × 43 3 × 42 × 65 |
| Calf Pillow | 104 | higher density polyurethane foam | 1.8 to 1.9 1.44 to 2.28 | 30 to 38 24 to 46 | 2.5 × 7 × 35 2 × 5.6 × 43 3 × 8.4 × 65 |
| Heel Cushion | 106 | vertical cell polyurethane foam | 1.1 to 1.25 0.88 to 1.5 | 12 to 16 9 to 20 | 2.5 × 19 × 35 2 × 17 × 43 3 × 21 × 65 |
| Base Structure | 108 | Densificated polyurethane foam | 2 to 2.3 1.6 to 2.76 | 20 to 25 16 to 30 | 5.5 × 35 × 80 4.4 × 28 × 64 6.6 × 42 × 96 |
| Core Layer | 110 | visco-elastic polyurethane foam | 2.7 to 3.3 2.16 to 3.96 | 9 to 15 7 to 18 | 3.5 × 20 × 35 2.8 × 16 × 43 4.2 × 24 × 65 |

Firmness or IDF (indentation force deflection) is measured in terms of pounds of force according to the ASTM #D3574 standard which specifies the force required to deflect a 15"×15"×4" thick piece of material 25% (i.e., 1") of the original thickness (i.e., 4") using an eight inch diameter indentation foot.

A commercially available example of synthetic latex foam includes Qualatex Type M20375BN Foam manufactured by Carpenter Company located in Richmond, Va. A commercially available example of higher density polyurethane foam includes Type CMX30185GA Foam manufactured by Carpenter Company. A commercially available example of vertical cell polyurethane foam includes Type CX11115WT Foam manufactured by Carpenter Company. A commercially available example of densificated polyurethane foam includes OMALON Foam (Type CDX20215RS Foam) manufactured by the Carpenter Company. A commercially available example of visco-elastic polyurethane foam includes Type VX9300BG Foam manufactured by the Carpenter Company. Other similar practicable foams are available from Fagerdala World Foams AB of Gustaysberg, Sweden. Other materials besides foam may be used. For example, an elastic or an inelastic bladder filled with fluids (e.g., liquids and/or gases) may be used for some or all of the components. Note in some embodiments, foam materials that allow airflow through the entire mattress may be selected to facilitate ventilation for temperature and moisture control.

The top layer 102 may have an elongated parallelepiped shape that has sufficient length to extend over the scapular zone 112, the sacrum/ischium/trochanter zone, and the thigh zone. In some embodiments, the end edge of the top layer 102 (closest to the heel end of the mattress) may be cut at an angle (e.g., downward sloping at 45 degrees) to mate flush with a trapezoidal shaped calf pillow 104. The calf pillow 104 may have a relatively short length and a parallelepiped shape that only extends over the calf zone 118. By supporting the calves with relatively firmer material, the heels are effectively suspended and off-loaded. In some embodiments, the calf pillow 104 may have trapezoidal cross-sectional shape with angled edges.

The heel cushion 106 may have an irregular shape wherein the height or thickness varies over the length of the heel cushion 106. In some embodiments, the heel cushion 106 may have an increasing or decreasing thickness from the head end of the mattress 100 to the foot end of the mattress 100. In some embodiments, the sides of the heel cushion 106 may not be perpendicular to the major surfaces of the heel cushion 106. This shape allows the heel cushion 106 to sit on the foot end of the base structure 108 (which is sloped as shown in the drawings) and to maintain flush contact with the side of the calf pillow 104. Further, this shape also allows the heel end of the mattress 100 to have an even vertical edge despite the slope of the foot end of the base structure 108. In some embodiments where a trapezoidal shaped calf pillow 104 is used, the edge of the heel cushion 106 (closest to the head end of the mattress) may be cut at an angle (e.g., upward sloping at 45 degrees) to mate flush with the trapezoidal shaped calf pillow 104.

The base structure 108 of the example mattress 100 has an irregular shape. There is a well or cut-out that spans the full width of the mattress 100 in the top surface of the base structure 108. The well has a trapezoidal cross-sectional shape and is disposed starting approximately thirty percent of the total length of the mattress 100 from the head end. In other words, in some embodiments, at approximately 25.5" from the head end of the mattress 100, the top surface of the base structure 108 angles downward at approximately 45 degrees to a vertical depth of approximately 3.5", continues horizontally for approximately 13", and then angles upward at approximately 45 degrees until the 5.5" height is reached. The top surface of the base structure extends approximately another 15.5" horizontally toward the foot end of the mattress 100 at the 5.5" height and then slopes downward at an approximately 7.5 degree angle for approximately 19" to the end of the base structure 108. The heel end of the base structure 108 is approximately 3" thick. The downward slope of the base structure 108 at the foot end of the mattress 100 allows the heels to be more easily suspended by the calf pillow 104. It will be understood that the dimensions and angles provided are merely illustrative examples and that other dimensions and angles may be used.

The well in the base structure 108 is approximately 3.5" deep and approximately 20" wide at the top and approximately 13" wide at the bottom. The well is specifically adapted to receive the core layer 110 such that when the core layer 110 is properly inserted into the well, the top surface of the base structure 108 is level and even with the top surface of the core layer 110. In addition, when the core layer 110 is properly inserted into the well, a smooth, level surface is available to make flush contact with the lower surface of the top layer 102. As will be discussed below with respect to FIG. 7, other mating core layer and well shapes and dimensions may be used.

In some embodiments, the mattress components 102, 104, 106, 108, 110 are assembled and held together by a fitted liner that surrounds the assembly but is stretchable in all directions to avoid suspending or "hammocking" the user. Alternatively, or in addition, the mattress components 102, 104, 106, 108, 110 may be fastened together permanently via, for example, a bonding agent, adhesive, or a heating process or non-permanently via, for example, hook and loop material or other releasable fastener.

In some embodiments, the liner may be formed from a gas permeable material that prevents liquids from passing through but allows gases to pass. Such a liner may be used to flow temperature-controlled air through the mattress to the patient to help control the patient's temperature or moisture level. In some embodiments, the liner may further have non-permeable sides to better direct airflow up though the mattress 100.

In some embodiments, in addition to any liner, any sheets or covers or "fire safety socks" used with the mattress of the present invention are stretchable in all directions to avoid suspending or "hammocking" the user and to avoid interfering with the support of the mattress itself.

Turning now to FIG. 5, the dynamic off-loading function of the mattress 100 is explained in more detail and illustrated using a close-up, cross-sectional view of the core layer 110 under load. The partial cross-sectional view of the mattress 100 is taken along line A—A in FIG. 2.

The top layer 102 is constructed from a material that is relatively less dense and is adapted to easily contour to the patient's body with minimum pressure. In contrast, the material selected for the core layer 110 is firmer and denser. This material is adapted to provide support for the patient's weight. The material selected for the base structure 108 falls between the conforming top layer 102 and the firmer core layer 110 in terms of density and support. These three components are adapted to interact with each other and the weight of the patient to maintain maximum oxygen saturation in the tissue between the mattress and the boney prominences of the sacrum/ischium/trochanter.

Figure 5A:
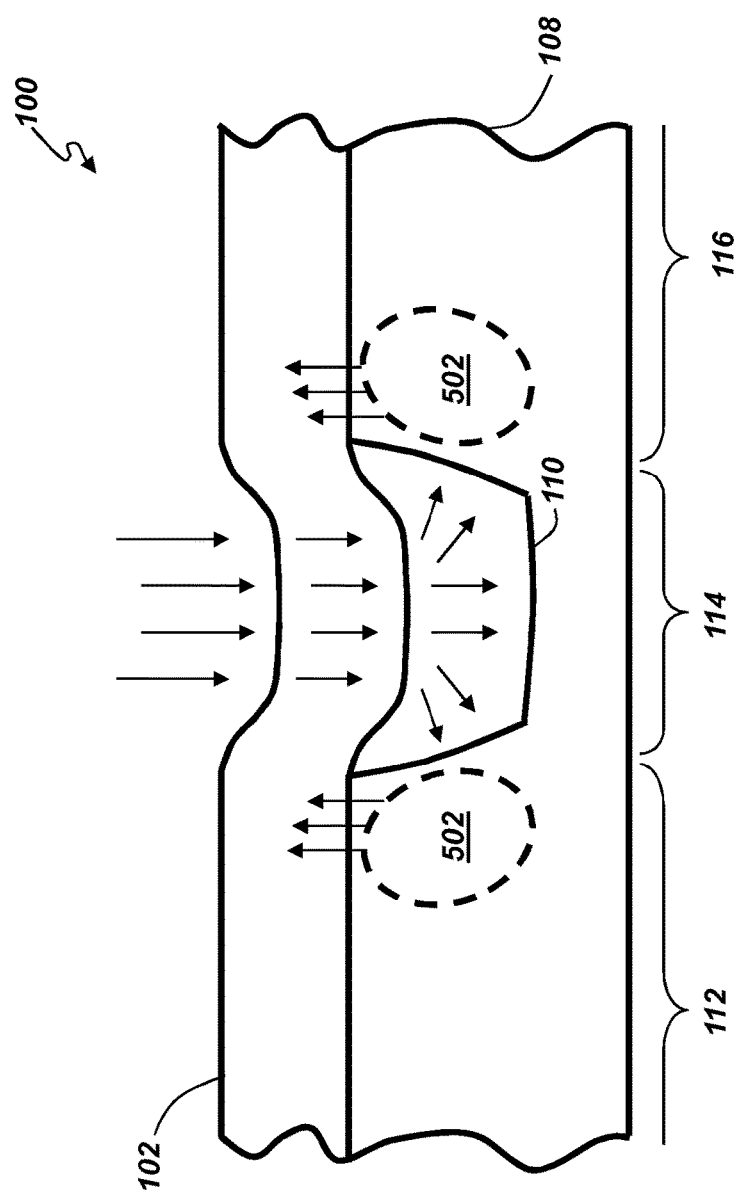
FIG. 5A is a close-up cross-sectional partial side view depicting a portion of an example mattress according to embodiments of the present invention.

As the patient's weight bears down on the top layer 102, some amount is supported and some weight is passed to the core layer 110 as represented by the downward pointing vector arrows and the deflection of the top layer 102 and the core layer 110 shown in FIG. 5A. The sloped edges of the trapezoidal shaped core layer effectively translate some component of the downward force in a lateral direction as represented by the more horizontal pointing vector arrows. The sloped edges are thereby distended and forced to push out laterally into the base structure 108. The volumes of the base structure proximate the core layer 110 indicated by the ovals drawn in phantom and labeled with reference numeral 502 are compressed by the laterally distended core layer 110.

The compression of these volumes 502 increases the density of base structure 108 proximate the core layer 110 by an amount related to the amount of weight bearing on the sacrum/ischium/trochanter zone 114. These volumes 502 of increased density provides additional support up to the patient in the scapular zone 112 and the thigh zone 116 as indicated by the upward pointing vector arrows. Thus, the effect of the mattress' structure and components' relative densities is to transfer pressure on the sacrum/ischium/trochanter zone 114 to the scapular zone 112 and the thigh zone 116 in proportion to the amount of weight brought to bear on the sacrum/ischium/trochanter zone 114. In other words, the more weight applied to the sacrum/ischium/trochanter zone 114, the more weight that can be supported by the adjacent volumes 502 of the scapular zone 112 and the thigh zone 116. The net effect is that the weight applied to the sacrum/ischium/trochanter zone 114 is dynamically off-loaded to the scapular zone 112 and the thigh zone 116.

The dynamic off-loading aspect of the present invention allows the same mattress 100 to be practicably used with different patients of different weights and widely varying body shapes and features. Further, the dynamic off-loading capability allows the mattress 100 to adjust to a patient's shifting weight and positions (e.g., prone, supine, side-laying) and/or from the use of an elevating support frame.

Figure 5B:
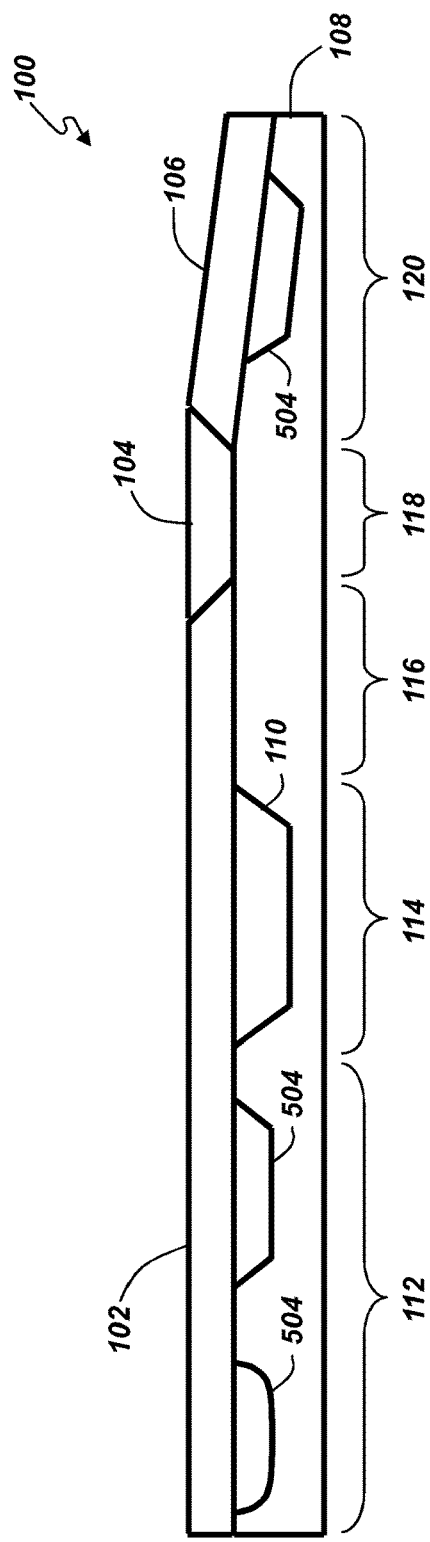
FIG. 5B is a side view depicting an example mattress according to alternative embodiments of the present invention.

More generally, the structure used to implement the dynamic off-loading aspect of the present invention may be referred to as a "pressure off-loading cradle." The pressure off-loading cradle includes a well in a base structure and a mating core layer shaped to translate downward pressure into lateral compression of adjacent base structure zones to provide additional support to body parts adjacent the part experiencing higher pressures. One or more pressure off-loading cradles can be formed in any mattress or cushion designed to support a body. The pressure off-loading cradles can be located wherever higher pressures are experienced. In other words, the pressure off-loading cradles can be applied to other areas of the body that experience high pressure and thus, would benefit from extra support on adjacent areas. For example, in some embodiments, a pressure off-loading cradle may be placed under the shoulder blades, under the head, and/or under the heels. FIG. 5B depicts an example embodiment of a mattress with multiple additional pressure off-loading cradles 504 disposed at these locations that correspond to bony prominences and/or higher interfacial pressure body regions. Note that the pressure off-loading cradles 504/110 may be of different sizes shapes, and orientations, and may be constructed of the same or different materials with the same or different densities and IDF ratings.

Figure 6:
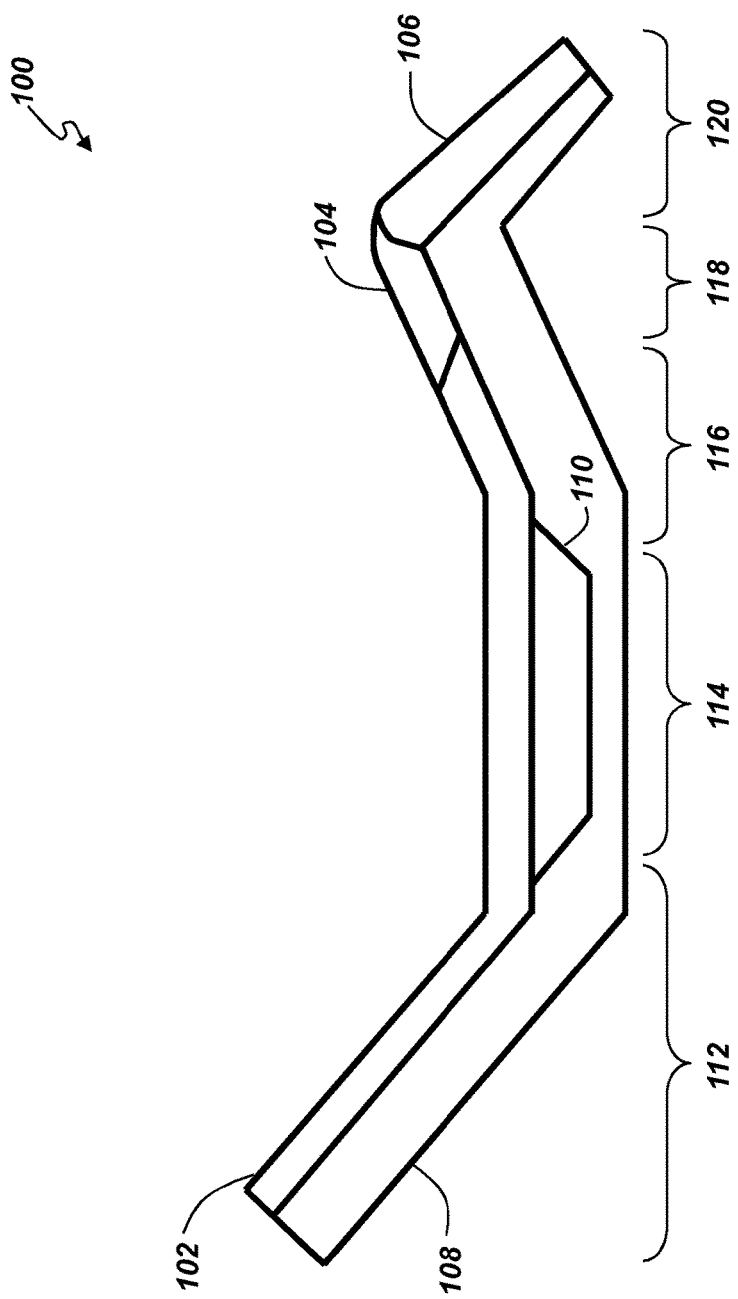
FIG. 6 is a side view depicting an example mattress in an inclined position according to embodiments of the present invention.

FIG. 6 illustrates a side view of the example mattress 100 as it may be supported by an elevating support frame. Note that the scapular zone 112 is inclined at approximately 45 degrees. Thus, as a result of the incline, some amount of the weight of the patient is shifted to the sacrum/ischium/trochanter zone 114. The increased weight at the sacrum/ischium/trochanter zone 114 means that the mattress will react by becoming more supportive (e.g., denser or firmer) in the scapular zone 112 and the thigh zone 116. Elevating support frames are typically adjustable though a range of incline angles. The mattress 100 of the present invention is adapted to adjust proportionately the off-loading support provided by the zones adjacent the sacrum/ischium/trochanter zone 114. In other words, as the incline angle changes, the amount of off-loading support changes in response to the shift of the user's weight to prevent blood flow restrictions.

In some embodiments, the present invention may be used in other body supporting systems. For example, portions of the sacrum/ischium/trochanter zone 114 and adjacent zones may be used in a wheel chair, desk chair, recliner, or couch. The mattress of the present invention may be used, for example, on a standard bed frame, a gurney, a hospital bed, an ambulance bed, an operating table, as a body support in a hyperbaric chamber, and in numerous other applications.

Figure 7:
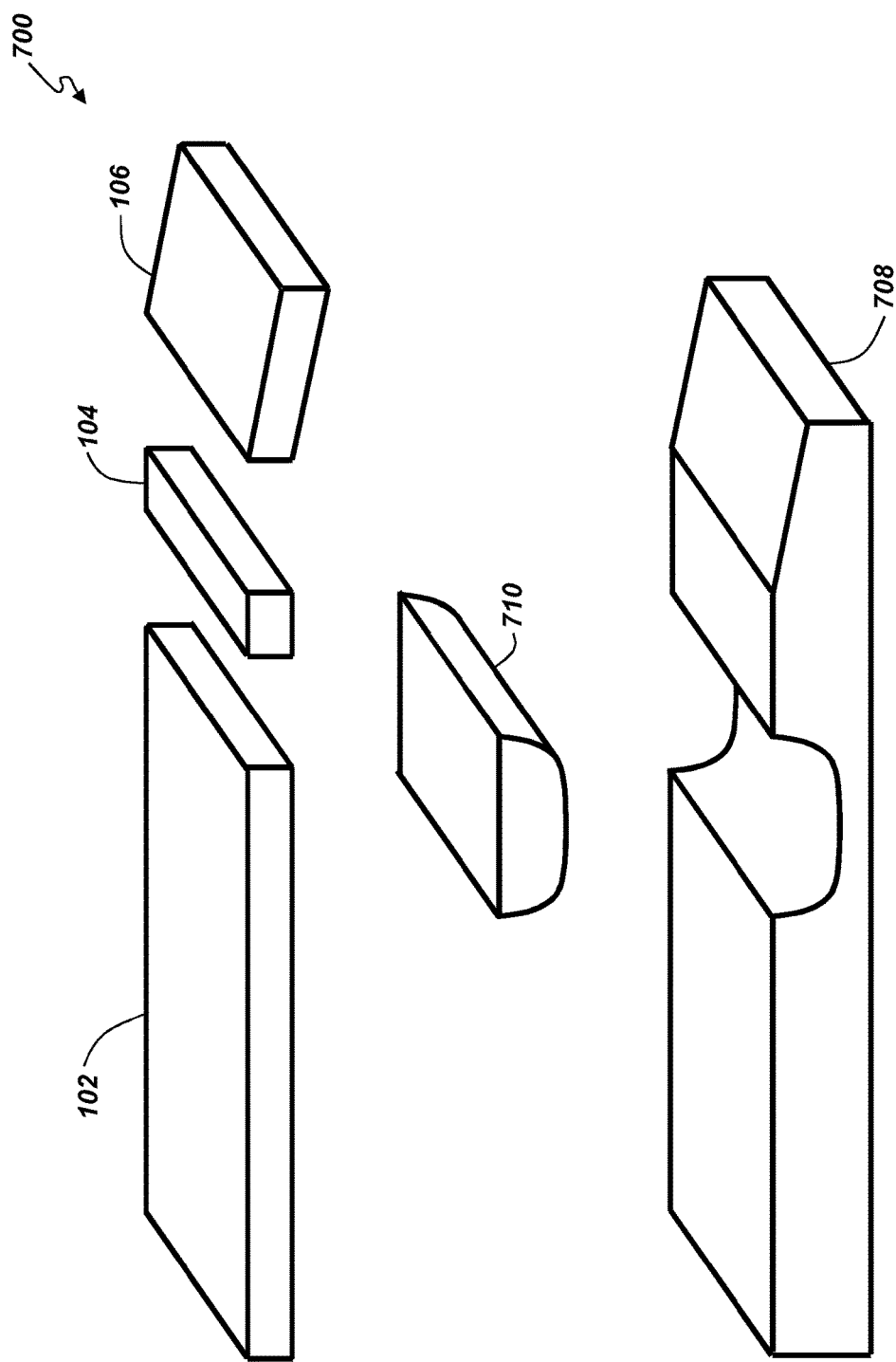
FIG. 7 is an exploded perspective view depicting a second example mattress according to embodiments of the present invention.

Turning to FIG. 7, an alternate example pressure off-loading cradle embodiment of a mattress 700 according to the present invention is illustrated in exploded perspective view. This example mattress 700 includes a well in the base structure 708 that has a parabolic shape and the mating core layer 710 has a matching parabolic shape. Other shapes are possible but the desired aspect of whatever shape is selected is that downward force on the top surface of the core layer 710 is translated into lateral expansion of the core layer 710 which compresses the laterally adjacent parts of the base structure 708.

Experimental Results

The performance of an example embodiment of the mattress of the present invention was tested in comparison to prior art mattresses to determine the relative ability of the mattresses to avoid blood flow restrictions at higher interfacial pressure areas. The prior art mattresses tested included an alternating pressure mattress called the microAIR Therapeutic Support System manufactured by Invacare Corporation of Cleveland, Ohio which alternates inflation and deflation of air cells to constantly change the points of pressure. A low air loss mattress, which supports a patient on air-filled cells while circulating air across the skin to reduce moisture and to help maintain a constant skin interface pressure, was also tested. Both of the prior art mattresses are significantly more expensive to manufacture and maintain than the mattress of the present invention. In addition, unlike the mattress of the present invention, these prior art mattresses also include powered components.

The average oxygen saturation in four higher interfacial pressure sensing areas (scapula, sacrum, ischium, and heel) was measured over a period of time while a test subject was reclined in two different positions: supine (horizontal) and inclined at 30 degrees. A cerebral/somatic Invos Oximeter, Model 5100C manufactured by Somanetics Corporation was used to measure deep oxygen saturation percentages. An FSA Pressure Mapping Mat, model number UT3010-7084, manufactured by Vista Medical of Winnipeg, Manitoba Canada was used to confirm the location of the higher interfacial pressure areas where the deep blood oxygen saturation levels were measured according to the present invention.

In the supine position, using the alternating mattress, the following average oxygen saturation measurements were made: scapula: 85.55%; sacrum: 88.70%; ischium: 86.41%; and heel: 50.07% for a total average oxygen saturation of 77.68%. In the inclined position, using the alternating mattress, the following average oxygen saturation measurements were made: scapula: 87.34%; sacrum: 89.07%; ischium: 89.50%; and heel: 53.17% for a total average oxygen saturation of 79.77%.

In the supine position, using the low air loss mattress, the following average oxygen saturation measurements were made: scapula: 84.98%; sacrum: 95.00%; ischium: 89.78%; and heel: 44.79% for a total average oxygen saturation of 78.64%. In the inclined position, using the low air loss mattress, the following average oxygen saturation measurements were made: scapula: 83.97%; sacrum: 95.00%; ischium: 91.79%; and heel: 47.61% for a total average oxygen saturation of 79.59%.

In the supine position, using a mattress according to the present invention, the following average oxygen saturation measurements were made: scapula: 86.81%; sacrum: 95.00%; ischium: 94.59%; and heel: 53.39% for a total average oxygen saturation of 82.45%. In the inclined position, using a mattress according to the present invention, the following average oxygen saturation measurements were made: scapula: 82.48%; sacrum: 95.00%; ischium: 94.84%; and heel: 60.30% for a total average oxygen saturation of 83.16%.

The above data clearly indicates that the performance (in terms of maintaining oxygen saturation in critical higher interfacial pressure areas) of the mattress of the present invention is similar to or better than the more expensive, powered prior art mattresses.

Sensor and Monitoring System

Figure 9:
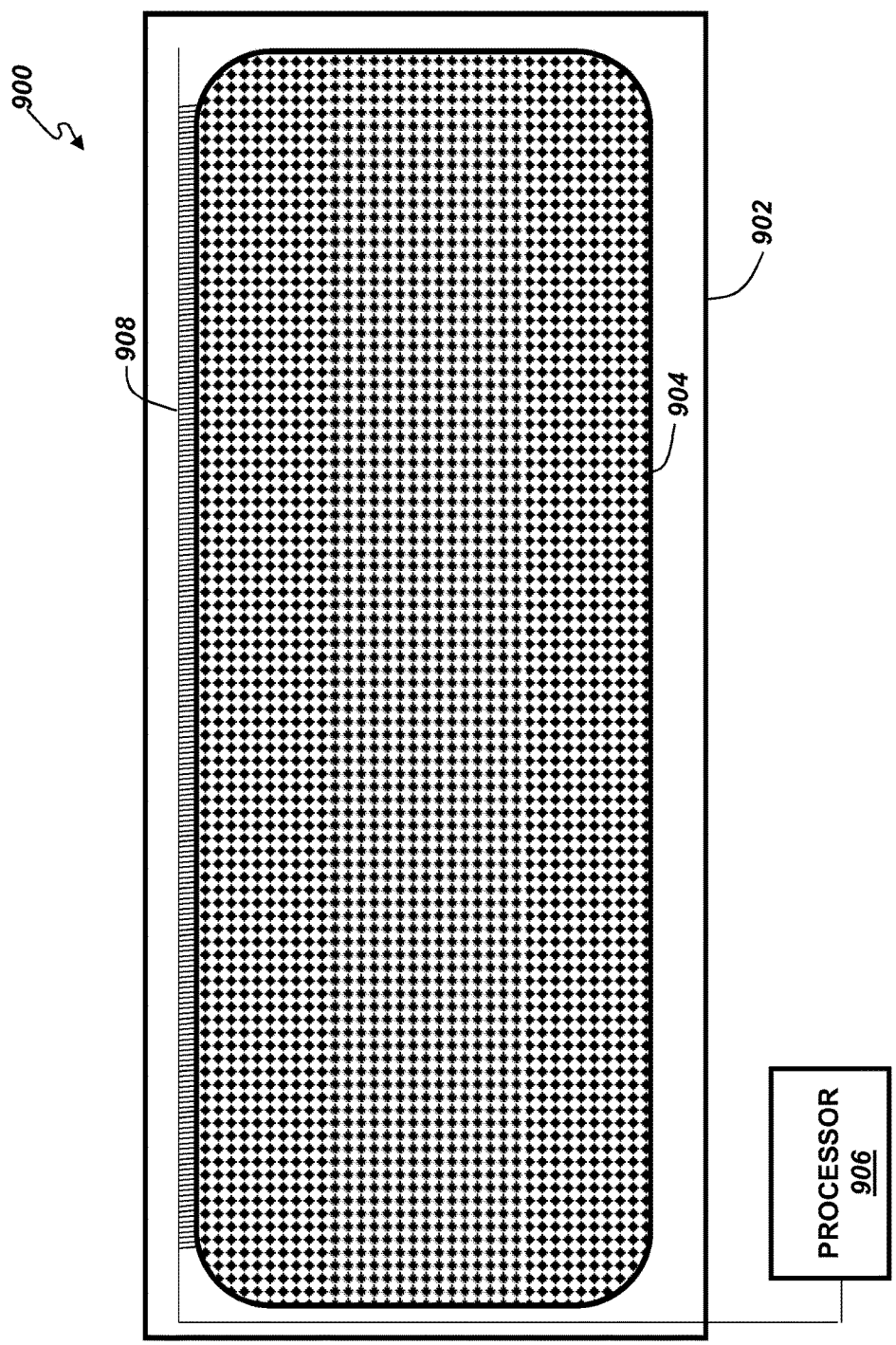
FIG. 9 is a schematic representation of a sensor and monitoring system according to embodiments of the present invention.

The present invention also provides methods and systems for monitoring the deep oxygen saturation levels in a patient laying on any type of mattress or support. Turning to FIG. 9, an illustration depicting a sensor and monitoring system 900 according to the present invention is shown. The system 900 includes a fabric pad or sheet 902 with a sensor array 904 (e.g., a regularly spaced, two-dimensional matrix of evenly aligned sensor nodes that covers the majority of the support surface as illustrated in FIG. 9) sown into or otherwise coupled to the sheet 902. In some embodiments, the sensor array 904 may be covered or enclosed in the sheet 902. In some embodiments as depicted in FIG. 9, the sensor array 904 may not be covered by the sheet 902 and may merely be supported by the sheet 902. In some embodiments, the sensor array 904 may be detachable from the sheet 902 to facilitate cleaning of the sheet. The sensor array 904 may be coated in a protective thin flexible plastic or other durable material so that the array 904 is not damaged by moisture or the weight of the patient. In some embodiments, the sensor array 904 may be formed integrally with a mattress and/or may include a pad or mat. In any of these embodiments, the sheet 902 and the sensor array 904 may be gas permeable to allow ventilation to flow up through the mattress, sheet 902 and the sensor array 904 to cool or dry the patient.

The sensor array 904 may be coupled to a processor 906 (e.g., a programmed computer) adapted to receive signals from the sensor array 904. An arrangement of flexible insulated wires 908 may be used to couple the sensor array 904 to the processor 906. The processor 906 may include one or more programs adapted to interpret the signals received from the sensor array 904. The signals may include information indicative of (1) the position of the patient on the array 904, (2) the distribution of the patient's weight (e.g., in terms of pressure) on the array 904, (3) the blood flow of the patient throughout the patient's body based upon, for example, a mapping of deep oxygen saturation levels throughout the patient's body, (4) the temperature of the patient throughout the patient's body, (5) the moisture level of the patient's skin contacting the array 904 or sheet 902, 902, etc.

This information may be combined to allow a user to have the system 900 monitor and determine the location of the patient on the mattress and, in particular, locate the patient relative to various different support zones of the mattress. This information may be displayed graphically on a computer monitor of the processor 906. The information may also be used to determine if an undesirable condition is occurring with respect to the interfacial environment. For example, the system 900 may be configured to detect a deep oxygen saturation level below a predefined threshold (e.g., approximately 50 MMhg to approximately 30 MMhg) at a particular location of the patient's body (e.g., the heels) for a predefined amount of time (e.g., approximately 15 minutes).

In another interfacial environment monitoring example, the system 900 may monitor the array for any location with an interfacial pressure over a predefined threshold value and then measure the deep oxygen saturation level at that location or adjacent area to determine if the deep oxygen saturation level is below a predefined threshold value. If so, the system 900 may determine that an undesirable condition or event is occurring. In yet another example, the system 900 may monitor for several conditions defined in a profile of an undesirable condition. For example, a reactive hyperemia event profile may be defined with a set of sensed conditions. The profile may include a number of parameters and threshold values for each parameter. As an illustration, the reactive hyperemia event profile may specify that if a change in body temperature is detected in excess of X degrees, a reduction of blood oxygen saturation level is detected in excess of Y MMhg, and a change in interfacial pressure of Z amount is detected, the system 900 may conclude that the patient has experienced a reactive hyperemia event. Likewise, other event profiles may be defined. For example, a bleeding profile may monitor for a temperature drop and a moisture level increase.

The system 900 may be configured to set off an alarm (e.g., an audible tone) if the undesirable condition or event is detected. In some embodiments, the graphical display may indicate the undesirable condition with an image of the patient and a colored area (e.g., red) that reflects the location and severity of the condition/event. The system 900 may provide instructions to a healthcare provider (e.g., a nurse hearing the audible tone) how to alleviate the undesirable condition. For example, in some embodiments, the system 900 may textually, verbally, audibly, and/or graphically suggest putting a pillow under the patient's calves to relieve pressure on, and increase blood flow to, the patient's heels.

In some embodiments, the system 900 may be coupled to a mattress or bed control system. In such embodiments, the system 900 may be adapted to activate features or capabilities of the mattress or bed control system to alleviate or address any undesirable conditions detected by the system 900. For example, if the system 900 detects a moisture level that could potentially cause shear stress on the patient's skin, the system may activate a fan or other air flow system to reduce the offending moisture level. In a powered mattress bed, the system 900 could be used to deflate or inflate a section of the mattress to address a low oxygen saturation level detected in a specific area of a patient's body which indicates a lack of blood flow. Likewise, the bed itself may be adapted to elevate or lower one or more mattress sections to address the undesirable condition in response to a signal from the system 900. In some embodiments, the system 900 may be adapted to control an electric, pneumatic, and/or hydraulic system capable of moving or rolling the patient to reduce pressure and increase the blood oxygen levels above the alarm set point.

Figure 10:
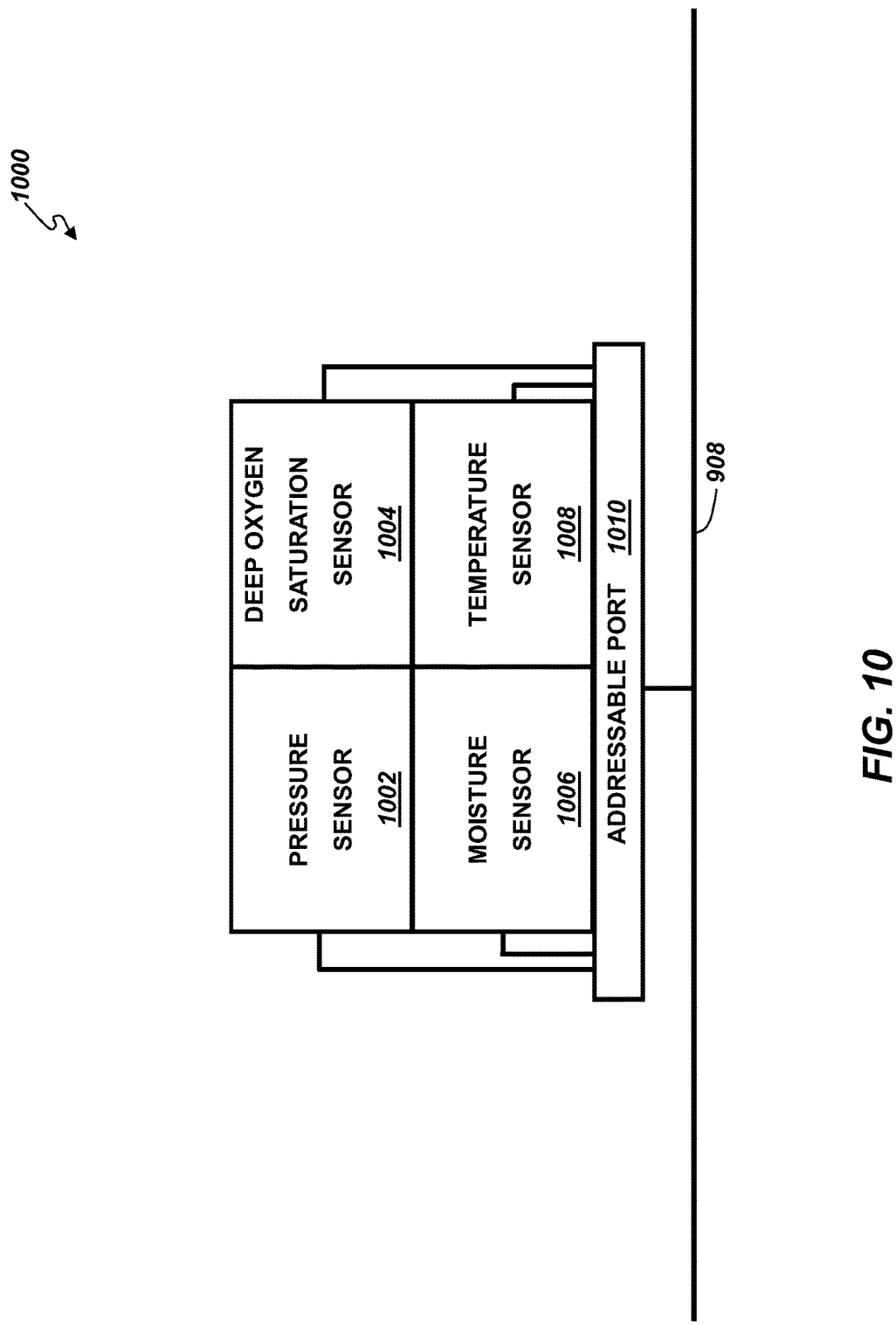
FIG. 10 is a schematic representation of an example embodiment of a node of a sensor array of a sensor and monitoring system according to embodiments of the present invention.

Turning to FIG. 10, an example node 1000 of the sensor array 904 is depicted. The depicted node 1000 may include a number of sensors such as a pressure sensor 1002, a deep oxygen saturation sensor 1004, a moisture sensor 1006, and a temperature sensor 1008. The individual sensors 1002, 1004, 1006, 1008 may be connected directly to the processor 906 or, as shown in FIG. 10, the sensors 1002, 1004, 1006, 1008 may be coupled to an addressable port 1010 which allows the node 1000 to be "read" to receive the respective information each sensor provides. Each node 1000 may be less than approximately one square inch in sensing area and, in some embodiments, may be less than one half a square inch in sensing area. In other embodiments, other size sensing areas may be used that are practicable. The nodes 1000 may be arranged in a regularly spaced array or matrix to allow the patient's position to be determined. In some embodiments, the nodes 1000 may be arranged in lines that run in the longitudinal dimension of the patients body and in other embodiments, the nodes 1000 may be arranged in lines that run in the lateral dimension of the patients body. In some embodiments, each node 1000 may only include a subset of the sensors 1002, 1004, 1006, 1008. In some embodiments, the nodes 1000 may be disposed on different layers of the sensor array 904. Thus, in some embodiments, the sensor array 904 may include a different layer for each sensor type. In some embodiments, the strands of different sensor types may be woven together to create the sensor array 904.

Figure 11:
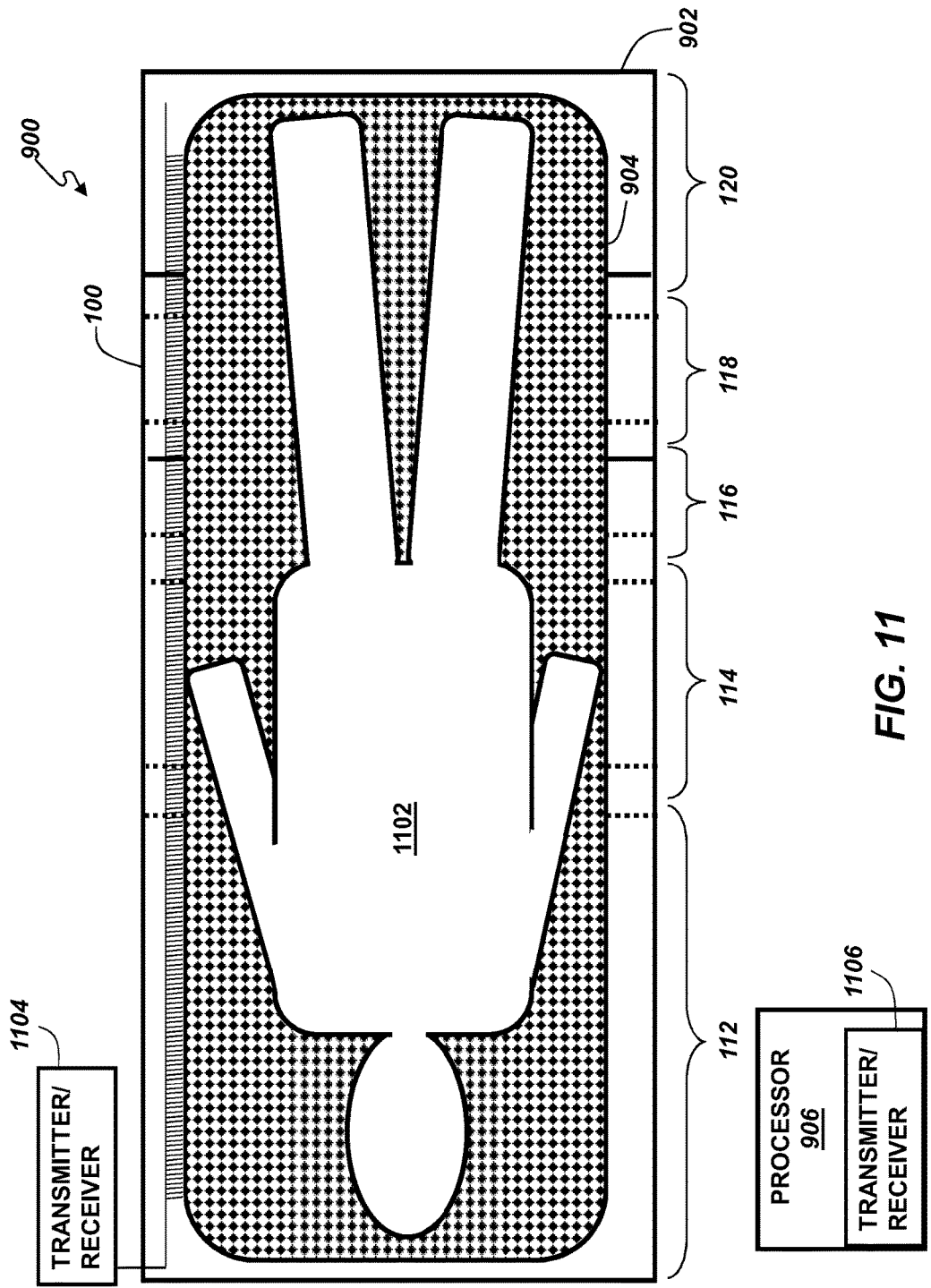
FIG. 11 is a schematic representation of an alternate embodiment sensor and monitoring system on a dynamic off-loading mattress according to embodiments of the present invention.

Turning now to FIG. 11, a representation of a patient 1102 is depicted on the system 900 of the present invention on a mattress 100 of the present invention. The relative position of the patient 1102 is correlated with the zones 112-120 of the mattress 100. In the example embodiment of FIG. 11, a wireless connection between the sensor array 904 and the processor 906 is illustrated. Both the sensor array 904 and the processor 906 include a wireless transmitter/receiver 1104, 1106, respectively that facilitates either two or one way communication between the sensor array 904 and the processor 906.

Figure 12:
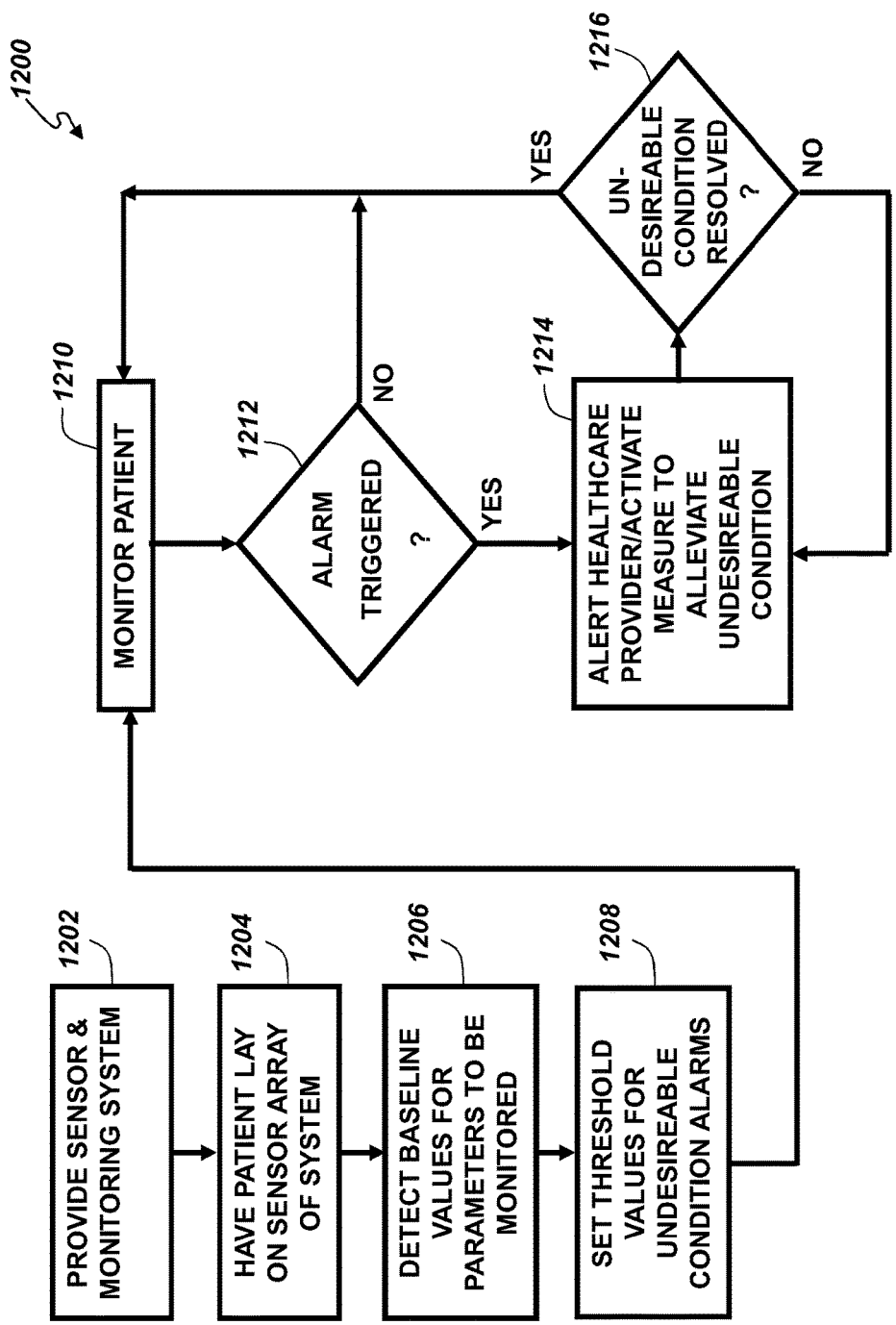
FIG. 12 is a flow chart depicting an example method of monitoring a patient for undesirable conditions according to embodiments of the present invention.

Turning now to FIG. 12, an example method 1200 of monitoring a patient for undesirable conditions is depicted in a flowchart. In Step 1202, the above described sensor and monitoring system 900 is provided on a suitable mattress such as the dynamic off-loading mattress 100 described above. In Step 1204, the patient lays down on the sensor array 904 of the system 900. In Step 1206, the system 900 is calibrated for the particular patient. The patient's overall weight is determined and the distribution of the patient's weight over the array 904 is measured. Measurements of the patient's normal deep blood oxygen saturation levels, temperatures, and moisture levels are made. Any abnormal conditions such as, e.g., existing wounds, bandaged areas, missing limbs, or other situations that could interfere with measurement are noted and entered into the software running on the processor 906. Baseline values of the various measurable interfacial environment parameters (e.g., deep blood oxygen saturation levels, interfacial pressure levels, temperatures, and moisture levels) for the particular patient are then determined along the length and width of the patients body.

In Step 1208, threshold values that would indicate occurrence of an undesirable condition or event are defined based on the baseline values determined in Step 1206. In some embodiments, event profiles based on several interfacial environment parameters reaching predefined thresholds may be defined. In Step 1210, monitoring of the patient begins. In Step 1212, the system 900 checks if any of the threshold values (e.g., that would indicate occurrence of an undesirable condition or event) have been reached and thus triggered an alarm. If not, flow returns to Step 1210 and monitoring of the patient continues. If so, flow proceeds to Step 1214 where a healthcare provider is altered to the undesirable condition or event and information regarding the situation is provided/displayed. In some embodiments, the system 900 may activate a measure to alleviate the undesirable condition. For example, the system 900 may control a bed frame or mattress to roll the patient or support the patient differently. In Step 1216, the system 900 checks to determine if the undesirable condition still persists or if the undesirable condition has been resolved. If the undesirable condition has not been resolved, flow returns to Step 1214 so that further steps may be taken to alleviate the undesirable condition. If the undesirable condition has been resolved, flow returns to Step 1210 and monitoring of the patient continues.

Mattress Design Methods

In some embodiments, the system 900 may be used to design a mattress 100 or other support with zones 112-120 adapted to maintain deep oxygen saturation levels above a desired threshold (e.g., approximately 50 MMhg to approximately 30 MMhg). The zones 112-120 may be constructed using different densities and types of materials to allow relative support of the patient's body which avoids blood flow restrictions.

Figure 13:
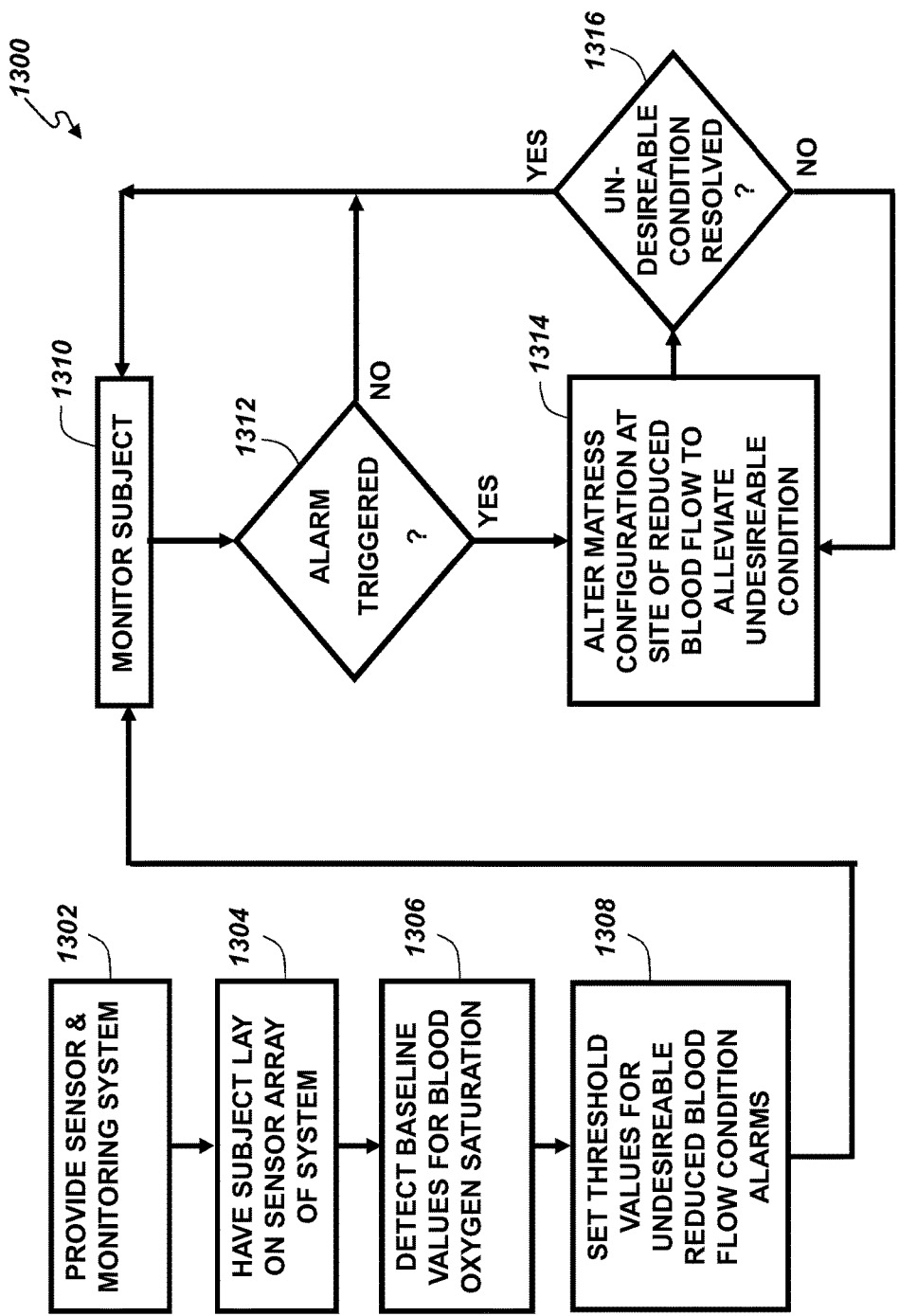
FIG. 13 is a flow chart depicting an example method of designing a mattress or support system that treats and reduces the incidence of pressure ulcers according to embodiments of the present invention.

Turning to FIG. 13, a flowchart depicting a method 1300 of using the system 900 to design a mattress is provided. In Step 1302, the above described sensor and monitoring system 900 is provided on a uniform foam pad mattress. In Step 1304, a test subject having a body representative of a standard intended user of the mattress, lays down on the sensor array 904 of the system 900. In Step 1306, the system 900 is calibrated for the test subject. The subject's overall weight is determined and the distribution of the subject's weight over the array 904 is measured. Measurement of the subject's normal deep blood oxygen saturation levels are made. Baseline values of the deep blood oxygen saturation levels and interfacial pressure levels for the test subject are then determined along the length and width of the subject's body. In Step 1308, threshold values for deep blood oxygen saturation levels at locations of higher interfacial pressure indicating reduced blood flow are set in the system 900. In step 1310, the subject is monitored while laying on the array for an extended period of time.

In Step 1312, the system 900 checks to determine if the reduced deep blood oxygen saturation threshold set in Step 1308 at locations of higher interfacial pressure has been reached. If not, the system 900 returns to monitoring the subject in Step 1310. If so, the subject is removed from the mattress and the mattress is modified to address the reduced deep blood oxygen saturation levels. By altering the materials, structure, densities, IDF, and other characteristics of the mattress at, or adjacent, the location corresponding to the reduced deep blood oxygen saturation levels, the mattress may be modified to improve the performance of the mattress with respect to avoiding causing pressure ulcers. For example, the pressure off-loading cradle structure described above may be used to support the bony prominences of the subject. Once the mattress is modified, the subject is returned to the mattress for further testing. In Step 1316, the system 900 determines of the reduced blood flow condition has been resolved by the modification. If not, further modifications may be made in Step 1314. If so, flow continues to Step 1310 for further testing. The method 1300 may iterate several times through the above-described test, modify, retest loop several times until an optimal mattress design is found. In some embodiments, the method 1300 may be terminated once no further improvement of the subject's blood flow while on the mattress can be achieved. In some embodiments, the method may be repeated for a wide range of test subjects to develop a mattress suitable for a wide variety of potential users.

In some embodiments, in addition to interfacial pressure and deep blood oxygen saturation, temperature and moisture many also be sensed and monitored between the test subject and the mattress. This additional information may be used to further refine the design of the mattress. For example, where higher moisture and/or temperature areas are detected in the interfacial environment (e.g., either of these parameters exceed a predefined threshold during a monitoring cycle), materials that allow increased ventilation may be selected.

The foregoing description discloses only exemplary embodiments of the invention. Modifications of the above disclosed apparatus and methods which fall within the scope of the invention will be readily apparent to those of ordinary skill in the art. For instance, while mattress examples are shown and described in the specification, the present invention may be applied to chair or couch seat cushions. In other words, for example, a wheel chair or recliner could include cushions with varying densities adapted to support a body while maintaining maximum blood flow/oxygen levels.

Accordingly, while the present invention has been disclosed in connection with exemplary embodiments thereof, it should be understood that other embodiments may fall within the spirit and scope of the invention, as defined by the following claims.

The invention claimed is:

1. A system for monitoring a patient to prevent and treat pressure ulcers, the system including:
    a sensor array configured to be disposed between a patient and a support surface, the sensor array including a plurality of individual nodes forming a two-dimensional matrix of nodes that is configured to cover at least a portion of the support surface, each individual node including at least a pressure sensor and an oxygen saturation sensor configured to transmit signals indicative of interfacial pressure and blood oxygen saturation levels in tissue in the patient's body, wherein strands of different sensor types are woven together to create the sensor array; and a processor coupled to the sensor array and configured to:
receive the signals transmitted by the nodes in the sensor array,
monitor the signals transmitted by the nodes in the sensor array to measure values of at least interfacial pressure and blood oxygen saturation of the patient,
determine whether a measured value exceeds a threshold value of at least one of interfacial pressure and blood oxygen saturation, and
determine an undesirable condition exists in response to the measured value exceeding the threshold value.

2. The system of claim 1 wherein one or more of the individual nodes have a sensing area of less than one square inch.

3. The system of claim 2 wherein one or more of the individual nodes are adapted to sense temperature levels.

4. The system of claim 2 wherein one or more of the individual nodes are adapted to sense moisture levels.

5. The system of claim 1 wherein the processor is configured to trigger an alarm if the processor determines an undesirable condition exists.

6. The system of claim 5 further comprising a display coupled to the processor and wherein the processor is configured to indicate a location of the undesirable condition that triggered the alarm using the display.

7. The system of claim 1 wherein the processor is configured to activate a measure to alleviate the undesirable condition if the processor determines an undesirable condition exists.

8. The system of claim 1, wherein blood oxygen saturation below a threshold value of blood oxygen saturation for a predetermined period of time is an undesirable condition.

9. The system of claim 8, wherein the predetermined period of time is 15 minutes.

10. The system of claim 1, wherein the oxygen saturation sensor is configured to measure blood oxygen saturation using near-infrared spectroscopy.

11. A method of monitoring a patient to prevent and treat pressure ulcers, the method including:

disposing a sensor array between a patient and a support surface, the sensor array including a two-dimensional matrix of individual nodes that cover at least a portion of the support surface, each individual node including at least a pressure sensor and an oxygen saturation sensor adapted to transmit signals indicative of at least interfacial pressure and blood oxygen saturation levels in tissue in the patient's body, wherein strands of different sensor types are woven together to create the sensor array;

receiving the signals transmitted by the nodes in the sensor array;

monitoring the signals transmitted by the nodes in the sensor array to measure values of at least interfacial pressure and blood oxygen saturation of the patient; and determining whether a measured value exceeds a threshold value of at least one of interfacial pressure and blood oxygen saturation; and determining an undesirable condition exists in response to the measured value exceeding the threshold value.

12. The method of claim 11 wherein one or more of the individual nodes have a sensing area of less than one square inch.

13. The method of claim 12 wherein one or more of the individual nodes sense temperature levels and transmit signals indicative of temperature levels, wherein monitoring includes monitoring signals indicative of temperature levels, and determining includes determining whether a monitored temperature level exceeds a threshold temperature level.

14. The method of claim 12 wherein one or more the individual nodes sense moisture levels and transmit signals indicative of moisture levels, wherein monitoring includes monitoring signals indicative of moisture levels, and determining includes determining whether a monitored moisture level exceeds a threshold moisture level.

15. The method of claim 11 further comprising triggering an alarm if a threshold value is exceeded.

16. The method of claim 15 further comprising displaying an indication of a location of the node that transmitted a signal indicative of a value or level that exceeded the threshold value.

17. The method of claim 11 further comprising activating a measure to alleviate the undesirable condition.

18. The method of claim 11, wherein the oxygen saturation sensor measures blood oxygen saturation using near-infrared spectroscopy.

* * * * *